(12) United States Patent
Mei et al.

(10) Patent No.: US 7,582,464 B2
(45) Date of Patent: Sep. 1, 2009

(54) MICROORGANISM AND THE PROCESS FOR PREPARATION OF PRAVASTATIN SODIUM

(75) Inventors: Mingquan Mei, Shanghai (CN); Xiaoming Ji, Shanghai (CN); Xiaoliang Gao, Shanghai (CN); Yi Chen, Shanghai (CN); Yan Li, Shanghai (CN); Yong Yao, Shanghai (CN); Zhonghao Zhuo, Shanghai (CN); Jing Xu, Shanghai (CN)

(73) Assignee: Shanghai Techwell Biopharmaceutical Co., Ltd, Shanghai (CN)

( * ) Notice: Subject to any disclaimer, the term of this patent is extended or adjusted under 35 U.S.C. 154(b) by 328 days.

(21) Appl. No.: 11/328,494

(22) Filed: Jan. 6, 2006

(65) Prior Publication Data

US 2006/0166340 A1 Jul. 27, 2006

Related U.S. Application Data

(63) Continuation of application No. PCT/CN2004/000699, filed on Jun. 28, 2004.

(30) Foreign Application Priority Data

Jul. 9, 2003 (CN) ............... 03 1 41475

(51) Int. Cl.
*C12N 1/20* (2006.01)

(52) U.S. Cl. .................. 435/252.1; 435/155

(58) Field of Classification Search ............ None
See application file for complete search history.

(56) References Cited

U.S. PATENT DOCUMENTS 5,830,695 A  11/1998  Serizawa et al.

FOREIGN PATENT DOCUMENTS

| EP | 215 665 | 3/1987 |
|----|---------|--------|
| WO | WO 96/40863 | 12/1996 |
| WO | WO 98/45410 | 10/1998 |
| WO | WO 00/46175 | 8/2000 |
| WO | WO 01/04340 | 1/2001 |

OTHER PUBLICATIONS

Nakagaito et al., IFO Res. Commun., 1993, vol. 16, pp. 109-124.*

* cited by examiner

*Primary Examiner*—Irene Marx
(74) *Attorney, Agent, or Firm*—Hamre, Schumann, Mueller & Larson, P.C.

(57) ABSTRACT

The invention provides a novel microorganism producing pravastatin sodium, as well as the method for producing pravastatin sodium by using this microorganism. *Micropolyspora roseoalba* CGMCC 0624 of the invention is highly tolerant to mevastatin sodium, and has a high transformation rate of mevastatin sodium, and can produce pravastatin sodium with a high efficiency and low cost.

1 Claim, 1 Drawing Sheet

MICROORGANISM AND THE PROCESS FOR PREPARATION OF PRAVASTATIN SODIUM

CROSS-REFERENCE TO RELATED APPLICATIONS

This application is a continuation of International application number PCT/CN2004/000699, filed Jun. 28, 2004 which claims priority to Chinese application No. CN 03141475.3 filed Jul. 9, 2003, the contents of both are herein incorporated in their entirety by reference.

FIELD OF THE INVENTION

The present invention provides a novel microorganism producing pravastatin sodium, as well as the method for producing pravastatin sodium by using this microorganism.

BACKGROUND OF THE INVENTION

Cardiovascular diseases are the major causes for human death. Both the morbidity and the mortality of cardiovascular diseases rank the first among all diseases. Medical studies have established that atherosclerosis is the primary pathological basis for cardiovascular diseases, and hyperlipemia is the leading factor for atherosclerosis. Therefore, the significance of lipid lowering drugs in the reduction of the incidence rate of cardiovascular diseases has attracted much attention, and researchers all over the world are dedicated to the development of lipid lowering drugs.

Among various lipid lowering drugs, a class of compounds of HMG-CoA reductase inhibitors, which were developed in the early 80's, has become the most active and rapidly developing field in studies of the cardiovascular drugs, due to their efficiency in the reduction of cholesterol levels, high selectivity for the inhibition of cholesterol synthesis, and low toxicity.

This kind of drugs are also known as statin drugs, including lovastatin, simvastatin, pravastatin, fluvastatin, cerivastatin, and atorvastatin, etc.

Compared to its analogs, pravastatin has unique tissue selectivity, selectively inhibiting the cholesterol synthesis in liver and small intestine, while only slightly inhibiting the cholesterol synthesis in other organs; furthermore, low toxicity is another advantage of pravastatin.

Pravastatin sodium (formula I) is produced from its prodrug, mevastatin (formula IIa) or mevastatin salts (formula IIb), by the hydroxylation in microorganisms.

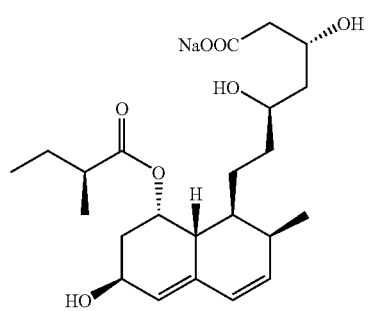

(I)

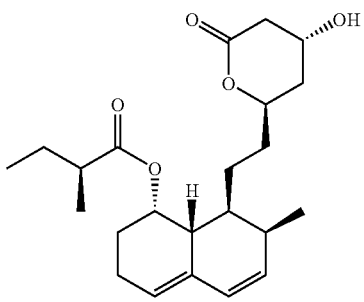

(IIa)

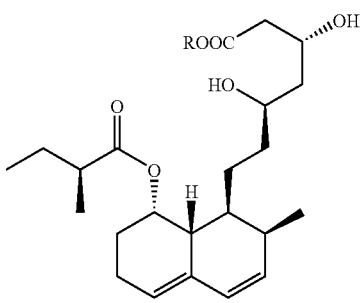

(IIb)

Mevastatin (IIa) has a low water-solubility, thus commonly transformed into mevastatin salts (formula IIb, wherein, R=alkali metals (for example, Na or K), alkaline earth metals, and NH$_4$) by adding some alkali.

In order to produce mevastatin sodium, the bio-transformation can be performed by a number of microorganisms, mainly including: some genera of the mould fungi (*Mortierella*, WO00/46175), *Norcardiaceae* (*Norcardia*, U.S. Pat. No. 5,830,695), *Actinomycesa madurae* (*Actinomadura*, WO96/40863), *Streptomyces* (*Streptomyces Carbopilus* EP215665, *Streptomyces exfoliatus* WO98/45410), and *Micromonospora*.

All of the aforementioned microorganisms, however, have a disadvantage during the producing process, i.e., the prodrug (mevastatin) of pravastatin is highly toxic to these microorganisms, especially to mould fungi, thus mevastatin concentration can only be maintained at a low level during industrialized production, and the transformation rate is relatively low and dramatically increases the cost for the transformation of pravastatin by microorganism.

In large-scale industrialized production, therefore, there is an urgent demand to developing microorganisms and the corresponding processes for the production of pravastatin sodium with a high efficiency.

SUMMARY OF THE INVENTION

The object of the present invention is to provide a microorganism and a method for producing pravastatin sodium with a high efficiency.

In the first aspect of the present invention, a strain of *Micropolyspora roseoalba* under the accession number CGMCC 0624 is provided.

In the second aspect of the present invention, the use of said *Micropolyspora roseoalba* for the production of pravastatin sodium is provided.

In the third aspect of the present invention, a method for the production of pravastatin or salts thereof is provided, which comprises the following steps:

(a) cultivating the *Micropolyspora roseoalba* under the accession number CGMCC 0624 at a temperature of 28-35° C. and a pH in the range of 6.8-7.5;
(b) adding mevastatin or its salts to maintain the concentration of mevastatin at 0.005-0.5wt % for 2-6 days;
(c) stopping the addition of mevastatin or salts thereof;
(d) isolating pravastatin or salts thereof.

In another preferred embodiment, the concentration of mevastatin or salts thereof is maintained at 0.01-0.05wt % in step (b).

In another preferred embodiment, step (b) is carried out for 3-5 days.

In yet another preferred embodiment, the isolation of pravastatin sodium is started after the concentration of mevastatin or salts thereof falls below 1 mg/l in step (d).

In still another preferred embodiment, the mevastatin or salts thereof in steps (b) and (c) is mevastatin sodium.

In another preferred embodiment, the isolated pravastatin salts in step (d) is pravastatin sodium.

MODE FOR CARRYING OUT THE INVENTION

Figure 1:
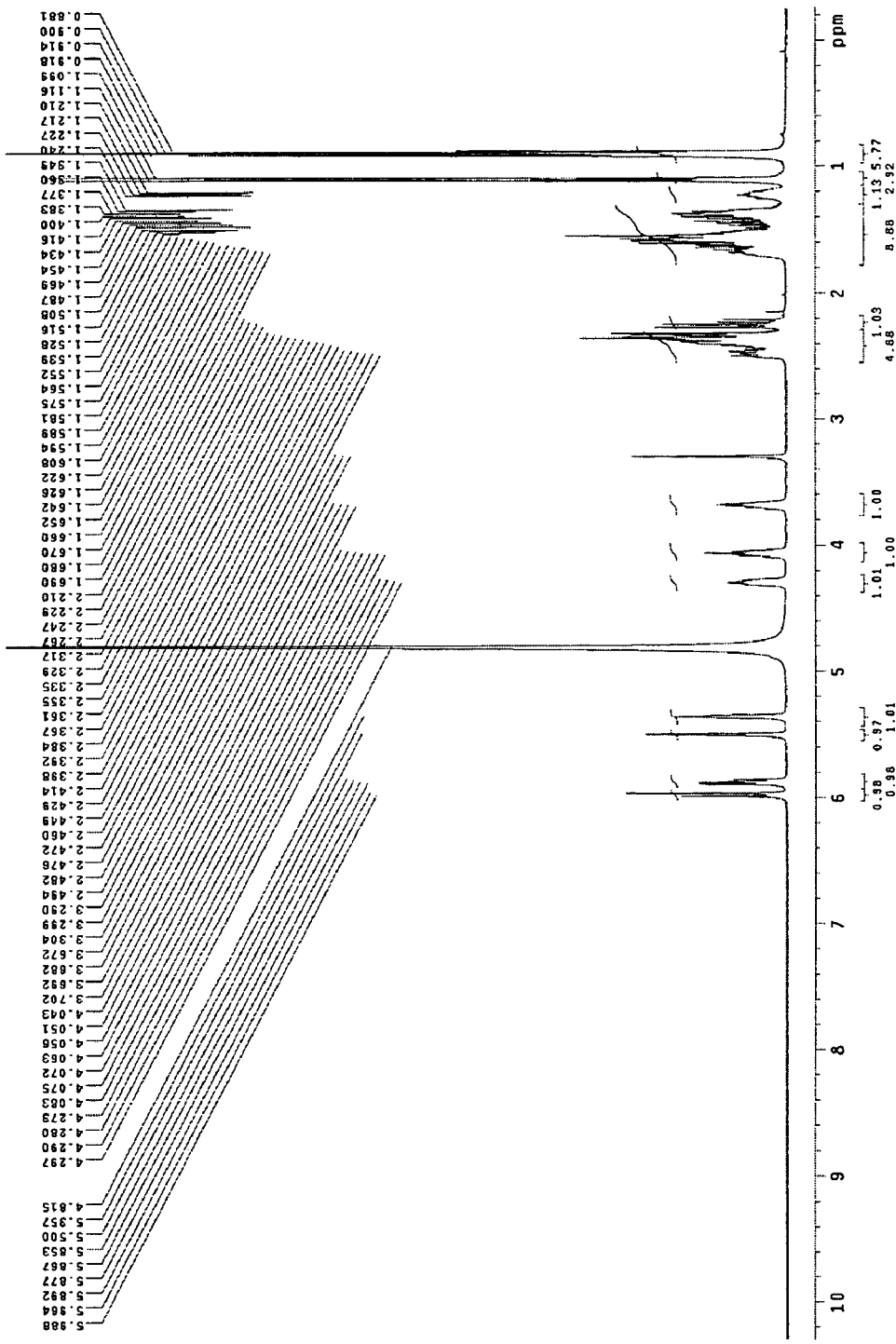
FIG. 1 illustrates the $^1$H NMR result of the pravastatin sodium prepared by the microorganism of the present invention.

Through extensive and intensive investigations, the present inventors have obtained a novel strain of microorganism, i.e. TW-9918, by conventional screening methods for microorganism. The microorganism tolerates high concentration of mevastatin and possesses extremely high transformation efficiency. The novel strain is designated as *Micropolyspora roseoalba*. The present invention was accomplished on the basis of this strain.

*Micropolyspora roseoalba* TW-9918 of the present invention has been deposited in China General Microbiological Culture Collection Center (CGMCC) (Beijing, China) on Aug. 29, 2001, under the accession number of CGMCC 0624.

The term "the strain of the present invention" or "the microorganism of the present invention", as used herein, refers to *Micropolyspora roseoalba* under the accession number CGMCC 0624, i.e., TW-9918.

The process of the present invention is essentially identical to those known in the art for the production of pravastatin sodium (e.g., the isolation and purification process of pravastatin sodium), except the conditions for fungi cultivation and fermentation.

The fermentation conditions for the strain of the present invention is similar to those for the ordinary *micropolyspora* strains. That is, fermentation is carried out with a culture medium containing carbon source, nitrogen source and trace elements with the pH range of 6.8-7.5 (preferably, 7.0-7.2) and at a temperature of 25-38° C. (preferably, 28-35° C.).

Some preferred culture media are as follows:

Yeast malt agar (ISP2) is used as slant culture medium, consisting of: malt extract 1.0%, yeast extract 0.4%, glucose 0.4%, agar 2.0%, pH 7.0-7.2.

Seed culture medium consists of: glucose 0.2-5.0%, yeast extract 0.05-0.5%, peptone 0.1-2.0%, $K_2HPO_4$ 0.02-0.1%, pH 7.0-7.2.

Fermentation medium consists of: glucose 1.0-5.0%, yeast extract 0.1-1.0%, peptone 0.5-2.0%, $K_2HPO_4$ 0.01-0.5%, $MgSO_4.7H_2O$ 0.01-0.05%, pH 7.0-7.2.

A preferred process of transforming mevastatin into pravastatin by TW-9918 strain is as follows:

TW-9918 is grown on slants at 28° C. for 7-10 days to produce mature inocula. The hyphae on the mature slants are inoculated into seed culture medium, and cultivated for 2-3 days at 28° C. in a shaker with a shaking rate of 210 RPM.

5-15% of the seed culture medium is inoculated into the fermentation culture, and cultivated in a shaker or a fermenter, at a temperature of 28-35° C. After 12-24 hours, the culture media are supplemented with 0.2-2.0% glucose every day, as well as mevastatin to maintain the mevastatin concentration of the medium at 0.005-0.5wt % (preferably, 0.01-0.05%). After 2-6 days (preferably, 3-5 days) of transformation cultivation, stop the supplementation of mevastatin, and stop the fermentation when mevastatin concentration in the medium falls below 1 mg/L.

The mycelia are removed by centrifugation and the supernatant is run through a hydrophobic resin, then the resin is washed with water. Pravastatin sodium is eluted with the mixture of ethanol/water solution or acetone/water solution, and the portion containing pravastatin is collected and concentrated. The concentrated solution is extracted with acetic ether, and then crystallized with ethanol/acetic ether to give pure pravastatin sodium.

The major advantages of the present invention are as follows:

The strain of the present invention is highly tolerant to mevastatin sodium, thus during the production process, the concentration of mevastatin sodium can be maintained at a relatively high level. The transformation rate for mevastatin sodium is high, resulting in the significant decrease in production costs.

The invention is further illustrated by the following examples. It is appreciated that these examples are only intended to illustrate the invention, but not to limit the scope of the invention. For the experimental methods in the following examples, they are performed under routine conditions, or as instructed by the manufacturers, unless otherwise specified.

EXAMPLE 1

The Isolation and Identification of the Strain Producing Pravastatin Sodium

1. The Isolation and Screening of the Microorganism

Soil samples collected at various locations in China were diluted $10^2$-$10^6$ times and were spread onto the plates. After 7-10 days incubation at a constant temperature of 28° C., about 1,500 strains were isolated for shaking vessel screening, among which 3 strains possessed the ability to transform mevastatin. The strain TW-9918, isolated from the soil sample from Ningbo, China, exhibited a high tolerance to mevastatin, and can transform mevastatin to pravastatin with a high efficiency.

2. The Identification of the Microorganism

Morphological Characteristics:

After 5-10 days growth on Stauton's agar and glucose asparagine agar, TW-9918 formed short chains with 3-12 spores on the aerial mycelia, with straight spore fibrillae. Substrate mycelia had tabulae and were ruptured, producing a few short spore chains. The spores were oval, 0.85×1.5 um, with smooth surface.

Cultivation Characteristics:

After 7-15 days of growth on seven media at 28° C., the characteristics of TW-9918 were as follows:

| Medium | Aerial mycelia | Substrate mycelia | Soluble pigments |
|---|---|---|---|
| Yeast malt agar (ISP2) | Grey | Light yellow | None |
| Stauton's agar | Grey | Light yellow | None |
| Glucose asparagine agar | Grey | Light yellow | None |
| Sucrose nitrate | Light Fresh | Sandstone yellow | None |
| Nutrition agar | Grey | Dirty yellow | None |
| Oat powder agar (ISP3) | Grey | Dark yellow | None |
| Potato agar | Grey | Light brown | None |

Chemical Analysis

Analysis of Cell Wall Components:

The cell wall of TW-9918 strain contained mdso-DAP (Diaminopimelic acid) and glycine (cell wall type IV).

Whole cell saccharide analysis:

The hydrolysis mixture of TW-9918 strain contains lactose and arabinose (saccharide type A).

Mycolic acid analysis:

TW-9918 strain did not contain mycolic acid.

Physiological and biochemical characteristics:

| Experimental Item | Results |
|---|---|
| D-glucose | + |
| L-arabinose | + |
| D-xylose | + |
| D-fructose | + |
| Sucrose | + |
| L-rhamnose | + |
| D-mannose | − |
| raffinose | + |
| L-inositol | + |
| Gelatin liquefaction | |
| Milk coagulation | − |
| Milk peptonization | + |
| Starch hydrolysis | − |
| Nitrate reduction | + |
| $H_2S$ production | − |
| Tyrosinase | − |

Results of Strain Identification:

The substrate mycelia of TW-9918 had tabulae and were ruptured; both aerial mycelia and substrate mycelia had short spore chains; cell wall was type IV, and saccharide was type A, having no mycolic acid. Thus, according to the principle of genus determination with morphological characteristics and cell wall's chemical components, TW-9918 belonged to *Micropolyspora*. Additionally, aerial mycelia of TW-9918 were grey; its substrate mycelia were light yellow, and possessed no soluble pigments. Consequently, according to the principle of species determination with cultivation characteristics and physiological and biochemical characteristics, combined with its physiological and biochemical characteristics, TW-9918 was similar to *Micropolyspora roseoalba*, thus belonging to *Micropolyspora roseoalba*.

At present, there are no reports of *Micropolyspora* strains applied to produce pravastatin sodium.

EXAMPLE 2

In this example, TW-9918 was used to produce pravastatin sodium.

50 ml seed medium was added into a 250 ml shaking vessel. The seed medium consisted of 2.0% glucose, 1.0% yeast extract, 1.0% peptone (pH 7.2). The seed stock solution was sterilized at 121° C. for 20 minutes. After the medium cooled down, TW-9918 was inoculated into the vessel, and cultivated in a shaker at 28° C. for 2 days, with a shaking rate of 210 RPM.

2 days later, 10 ml seed stock solution was respectively added into two 500 ml shaking vessels, each containing 100 ml fermentation medium, and cultivated in a shaker at 30° C., with a shaking rate of 290 rpm. The fermentation medium consisted of: glucose 2.0%, yeast extract 0.5%, peptone 2.0%, $K_2HPO_4$ 0.05%, $MgSO_4 \cdot 7H_2O$ 0.05%, pH 7.2, and was sterilized at 121° C. for 20 minutes. After 24 hours of cultivation, carbonhydrates were fed in; for glucose, the daily adding amount was 2.0%. The mevastatin content in the solution was measured by HPLC, and its concentration was maintained at 0.01%-0.05% by supplementing aqueous solution of mevastatin sodium. The cultivation was concluded after 4 days, with 0.6 g (3 g/L) mevastatin added altogether.

After the fermentation ceased, the mycelia were removed by centrifugation, leaving about 180 ml supernatant. The adsorption was performed with 100 ml HP-20 resin, which was washed with 500 ml distilled water after absorption; then the pravastatin sodium was eluted with 50% acetone. The portion containing pravastatin sodium was collected and concentrated; the concentrated solution was subjected to decolourization, acetic ether extraction, and ethanol/acetic ether crystallization, and finally gave 0.2 g pure pravastatin sodium.

EXAMPLE 3

In this example, TW-9918 was fermented in a 5 L automatic fermenter to produce pravastatin sodium.

3.5 L fermentation medium was added into a 5 L automatic fermenter, and sterilized at 121° C. for 20 minutes. After the medium was cooled down, 300 ml seed stock solution was inoculated into the fermentation, and the mixture was cultivated according to the methods in Example 2. The fermentation medium consisted of: glucose 2.0%, yeast extract 1.0%, peptone 2.0%, $K_2HPO_4$ 0.1%, and $MgSO_4 \cdot 7H_2O$ 0.05%.

Fermentation was carried out at a temperature of 30° C., with the aeration rate of 3 L/minute and a stirring rate of 300-500rpm. After fermenting for 18 hours, mevastatin sodium saline solution and glucose solution were continuously supplemented, and the mevastatin concentration was maintained at 0.03-0.05%. Transformation lasted for 96 hours, and 20 g (5.7 g/L) mevastatin was added altogether.

The transformation medium was purified according to the methods in example 2, and finally 7.6 g pravastatin sodium was obtained. The $^1H$ NMR result of the resulting pravastatin sodium is showed in FIG. 1, which is identical to that of pravastatin sodium standard.

Deposit of the Strain

*Micropolyspora roseoalba* TW-9918 of the present invention was deposited in China General Microbiological Culture Collection Center (CGMCC) (Beijing, China) on Aug. 29, 2001, under the accession number of CGMCC 0624.

The invention claimed is:

1. A biologically pure culture of strain *Micropolyspora roseoalba* whose accession number is CGMCC 0624, said culture is capable of producing pravastatin or salts thereof.

* * * * *